(12) United States Patent  
Pasha

(10) Patent No.: US 8,512,038 B2  
(45) Date of Patent: *Aug. 20, 2013

(54) DENTAL HIGH VOLUME SUCTION TUBE WITH PROTECTIVE CAP

(76) Inventor: Faheem Pasha, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/371,553

(22) Filed: Feb. 13, 2012

(65) Prior Publication Data

US 2013/0059265 A1     Mar. 7, 2013

Related U.S. Application Data

(63) Continuation-in-part of application No. 13/066,573, filed on Apr. 18, 2011, now Pat. No. 8,360,773.

(51) Int. Cl.
*A61C 17/06*     (2006.01)

(52) U.S. Cl.
USPC ............................................................. 433/96

(58) Field of Classification Search
USPC ................................ 433/91, 96; 604/904, 902
See application file for complete search history.

(56) References Cited

U.S. PATENT DOCUMENTS

| 950,109 | A | 2/1910 | Levkowicz |
| 1,184,922 | A | 5/1916 | Brownton |
| 2,130,406 | A | 9/1938 | Angell |
| 2,742,701 | A | 4/1956 | Berger |
| 3,256,885 | A | 6/1966 | Higgins |
| 3,373,492 | A | 3/1968 | Batch |
| 4,490,138 | A | 12/1984 | Lipsky et al. |
| 5,015,184 | A | 5/1991 | Perry et al. |
| 5,066,228 | A | 11/1991 | Doundoulakis et al. |
| 5,181,907 | A | 1/1993 | Becker |
| 5,380,245 | A | 1/1995 | Reiterman et al. |
| 5,690,487 | A | 11/1997 | Whitehouse et al. |
| 8,360,773 | B2 * | 1/2013 | Pasha ............................... 433/96 |

* cited by examiner

*Primary Examiner* — Ralph Lewis
(74) *Attorney, Agent, or Firm* — The Adams Law Firm

(57) ABSTRACT

A high volume suction tube for use in dentistry to remove detritus during oral procedures, such as providing a tooth filling, including a cap that alleviates tissue obstruction without impeding efficient suction and removal of the detritus.

25 Claims, 4 Drawing Sheets

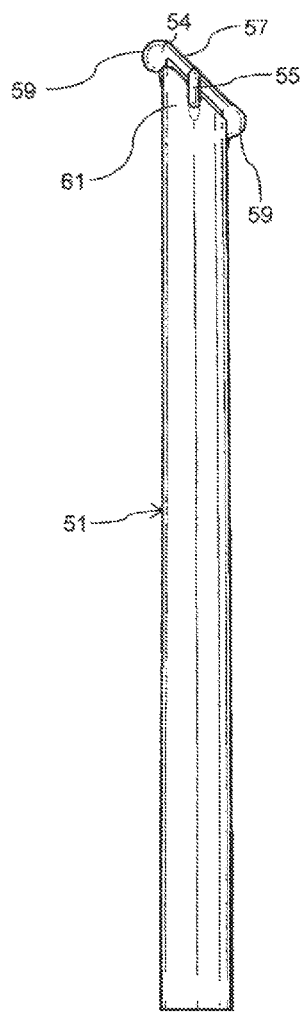 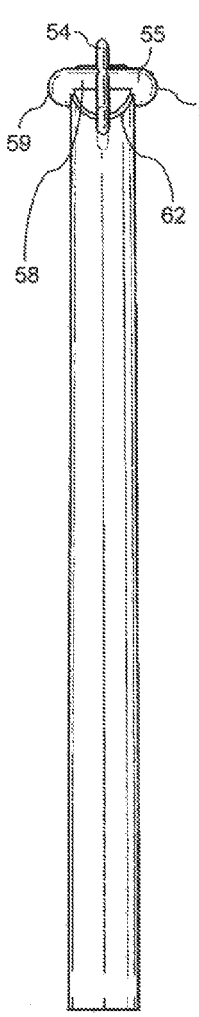 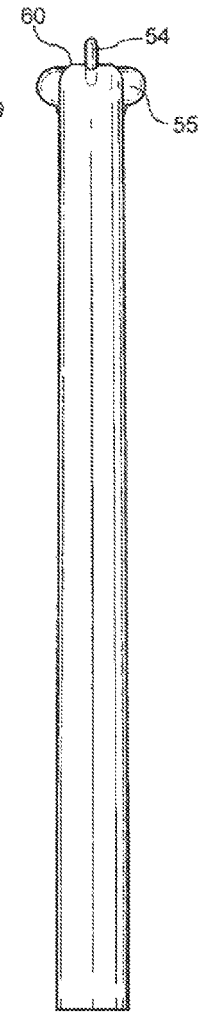 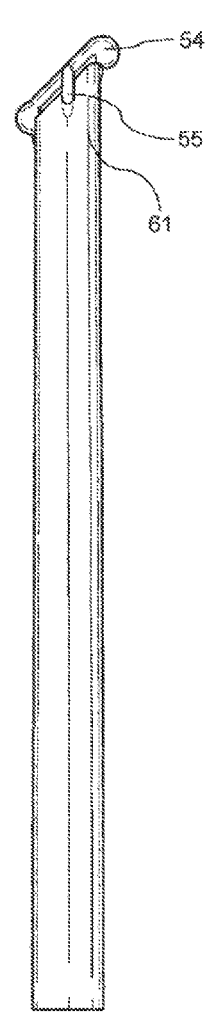
FIG. 5    FIG. 6    FIG. 7    FIG. 8
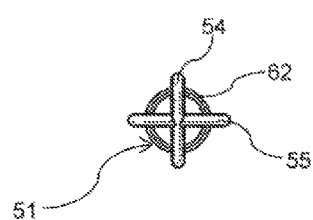 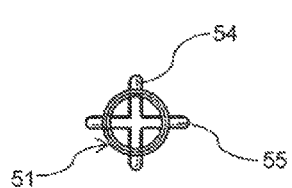
FIG. 9    FIG. 10

DENTAL HIGH VOLUME SUCTION TUBE WITH PROTECTIVE CAP

This application is a continuation-in-part of U.S. application Ser. No. 13/066,573 filed Apr. 18, 2011. The patent application identified above is incorporated herein by reference in its entirety to provide continuity of disclosure.

BACKGROUND OF THE INVENTION

The present invention is a cap and a tube for high volume dental suction. One end of the tube is designed to fit the cap.

High volume evacuation (HVE) suction devices are used during dental procedures to remove saliva and particles, such as plaque, calculus, parts of existing fillings and decayed tooth material. Such HVE suction devices include a suction tube having a distal (upper) suction end and a proximal (lower) discharge end. The discharge end of the suction tube connected via a hose and hose valve to a vacuum source. The distal (upper) end of the suction tube is inserted into a patient's mouth.

The HVE suction tube is typically made of polyvinyl chloride or polyethylene. Such tips are hard and the edges rather sharp, which can irritate the tissue of a patient's mouth.

The suction draws material into the opening and down the tube. If the tip contacts the patient's mouth tissue, it can suck the tissue into the tip, obstructing the suction. This is uncomfortable and can cause damage to the patient's mouth and make it more difficult for the dental user. Such HVE suction tubes can require constant manual adjustments to maintain efficient suction while in use and cause unpleasant sensations, bruising and anxiety to patients.

SUMMARY OF INVENTION

The present invention provides a protective suction cap and the specially designed HVE tube onto which it fits; the invention overcomes the aforementioned difficulties with existing HVE suction tubes.

The HVE tube of the invention includes a tube having a suction end and a discharge end and which can be used with or without the protective cap attached.

The invention can also be produced as one piece, with the cap permanently attached to the HVE tube. In a one-piece embodiment, the entire tube and cap may be molded from a plastic material that is resilient or semi-resilient, such as polyethylene.

The cap provides a gap between the suction end of the HVE tube and the oral tissue to simultaneously allow tissue retraction and suction in the working area of an oral cavity without causing trauma to fragile tissue.

A dental suction tube including at a distal end a cage-like structure comprising at least four vanes, each vane having a question-mark-like shape with a generally straight proximal section and a curved distal section, the straight section proximal end supported on the end of the dental suction tube and the distal ends of the curved sections of each vane attached to one another.

A high-volume evacuation tube used in dental procedures including a cap, the cap comprising a crown-shape, cage-like structure including at least three struts, each strut having a generally convex shape, the proximal end of each strut attached to the distal end of the tube and the distal ends of the struts attached to one another. In another embodiment the cap may have three convex curved arms connected at proximal ends to the tube and the distal ends to one another such that the cross-sectional area between the curved arms is greater than the tube cross-sectional area.

A dental suction tube including at a distal end a cruciate structure comprising two orthogonal cross members, the suction tube distal end edge formed at an acute angle to the longitudinal axis of the tube, the cruciate structure lying substantially in a plane parallel to the distal end edge, each of the cross members extending radially beyond the edge of the tube distal end edge, the radial portion beyond the edge of the tube distal end edge having a round shape, the edge of each round shape of the cross members attached to the two distal end openings.

BRIEF DESCRIPTION OF THE DRAWINGS

FIG. 5 is a first side elevation view of the embodiment shown in FIG. 4;

FIG. 6 is a front elevation view of the embodiment shown in FIG. 4;

FIG. 7 is a rear elevation view of the embodiment shown in FIG. 4;

FIG. 8 is a second side elevation view of the embodiment shown in FIG. 4;

FIG. 9 is a top plan view of the embodiment shown in FIG. 4;

FIG. 10 is a bottom end view of the embodiment shown in FIG. 4;

DETAILED DESCRIPTION OF THE INVENTION

Figure 1:
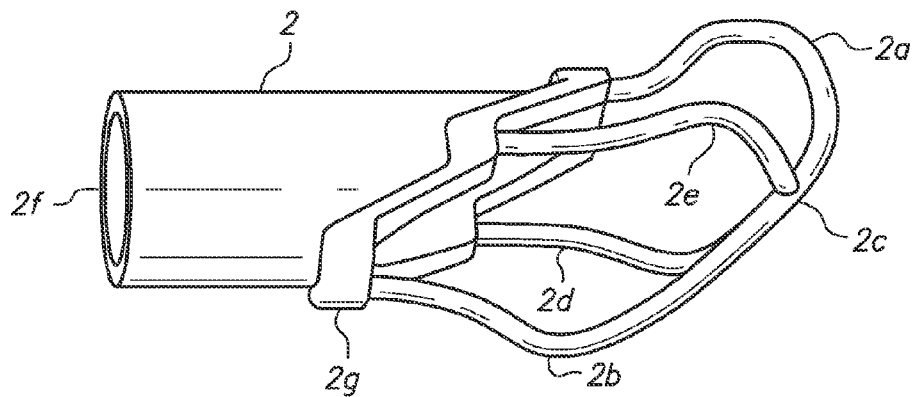
FIG. 1 is a right side view of the crown-shaped cap.
Figure 2:
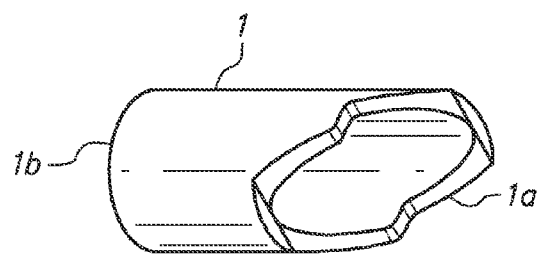
FIG. 2 is a right side view of the HVE suction tube of the present invention specially designed to fit onto the crown shaped cap by pressing the cap into the suction end of the HVE tube.
Figure 3:
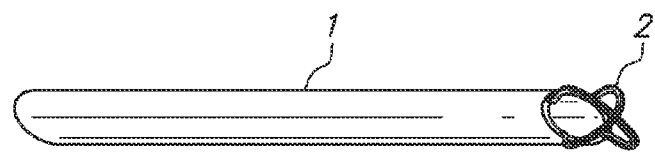
FIG. 3 is a perspective view of the HVE suction tube with crown shaped tip permanently attached on the suction end as one piece.

The present invention in the embodiments shown in the drawings dudes an HVE suction tube 1 having a suction or distal end 1a (see FIG. 3), and a discharge or proximal end 1b, the end 1b attached to flexible tubing that attaches to the source of suction. The distal end of the tube has a crown-shaped, cage-like cap or structure 2. The cap-like structure may be detachably connected to tube 1 at the distal end 1a as shown best in FIG. 1. Alternatively, in the embodiment shown best in FIGS. 3 and 3A, the cage-like structure may be integral with the tube 1, the tube and cap-like structure molded of plastic material such as polyvinyl fluoride or polyethylene, materials well known in the field of dentistry. The tube 1 typically has a length of 4-6 inches and an internal diameter of approximately ¼ inch with a wall thickness of approximately 1/32 inch. The distal end of tube 1, as seen best in FIGS. 1 and 2, is terminated to form an edge 1c in a plane that is acute to the longitudinal axis of the tube 1. As shown in FIG. 2, the edge may have steps with corresponding and complementary steps formed in the short attachment section 2g of the cage-like structure 2 to provide a secure support for the cap 2 on tube 1.

The cage-like structure or cap 2 as noted above has a short tubular section indicated at 2g fitted within the end of tube 1 in frictional engagement therewith. The cage-like structure 2 comprises in the embodiment shown four vanes or struts indicated at 2a, 2b, 2d, and 2e, although three vanes or struts may be employed depending on the plastic material chosen for forming the cap.

Figure 3A:
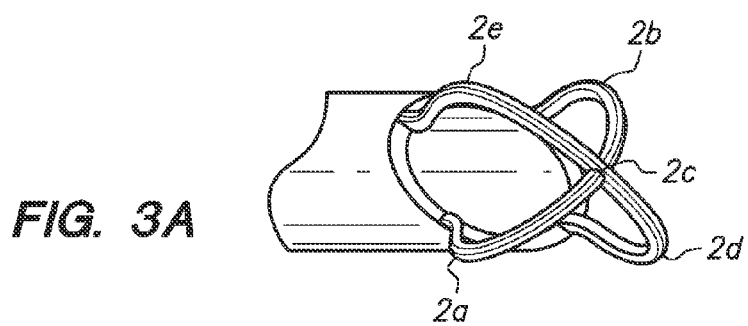
FIG. 3A is a close-up view of FIG. 3.
Figure 4:
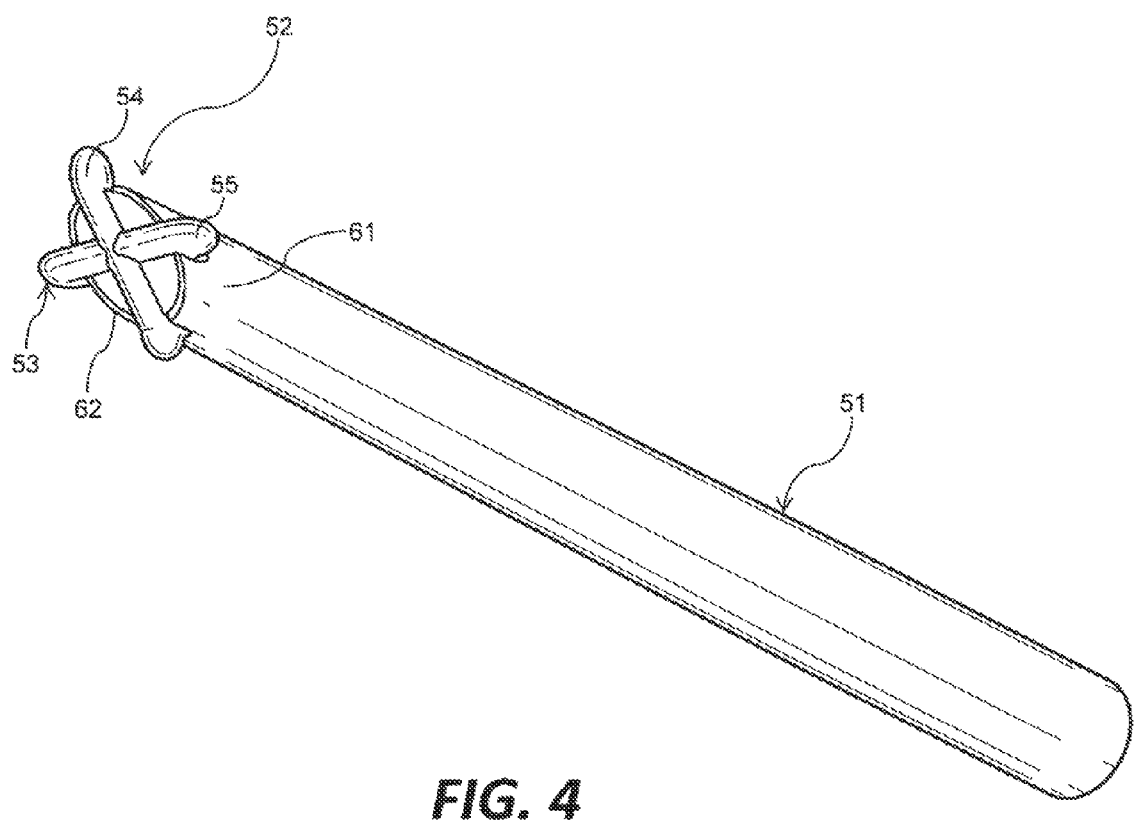
FIG. 4 is another embodiment of the invention showing an alternative cap construction comprising a cruciate structure.

Each of the vanes or struts 2a, 2b, 2d, 2e has a question-mark shape which include a short straight or slightly curved proximal section 2h and curved convex distal section. The proximal end of the proximal sections are attached to and may be integral with the ring portion 2g of the cap-like structure 2 that attaches to the distal end 1a of tube 1 as shown in FIG. 1 or at the tube edge as seen best in FIG. 3A. At the distal end of each distal section 2a, 2b, 2d and 2e, of the vanes or struts the ends are attached to the corresponding end of each of the other vanes or struts at 2c. It will be understood that each of the vanes may be molded in plastic as an integral structure. Each of the vanes may have a circular cross section as shown in FIG. 1 or a polygonal cross section as shown in FIG. 3A.

The vanes or struts of the cage-like structure or cap 2 have a diameter, as measured in a plane that is transverse to the axis of the tube that is greater than the inner diameter and/or outer diameter of tube 1. The cap-like structure or cap 2 extends axially or longitudinally from the distal end 1a of the tube 1a distance greater than the inner or outer diameter of tube 1.

It will therefore be seen that the area as measured between each pair of vanes or struts, in the aggregate, is greater than the cross-sectional area of tube 1. It will also be appreciated that the cage-like structure is slightly resilient such that when inserted into the patient's mouth, it may distort slightly but will prevent the oral tissue from blocking the distal open end of tube 1 or from being aggravated. The area is thus large enough for suction uptake of larger particles that may be generated during dental processes.

In operation, the distal end of the tube 1 with the cage-like cap 2 is inserted into the patient's mouth such that the cap is in contact with the patient's oral tissue. When suction is applied, the cap 2 will prevent or minimize any plugging of the end of the suction tube by tissue while still allowing suction to remove the unwanted materials from the oral cavity. The cap 2 thus eliminates the danger of the tissue being grabbed or forcibly pressed against the end of the tube which is frequent with existing dental suction tubes commonly used in dental practices today.

The embodiment shown in FIGS. 4-10 illustrates a tube, indicated at 51 that is substantially the same as tube 1 in the earlier embodiments. The tube has a cap indicated at 52 that may be integral with tube 51 or detachable (not shown). Cap 52 is positioned at the distal end 61 and comprises a cruciate structure indicated generally at 53 comprising two orthogonal cross members, struts, or arms 54, 55. The members 54, 55 are arranged orthogonally to one another and connected at their central portions to one another.

Tube 51 has a proximal end that is attached to a vacuum source through flexible tubing and a valve in a manner ell known to those having ordinary skill in the art. The distal end 61 is terminated at an acute angle to the longitudinal axis of tube 51 as seen best in FIGS. 5 and 8. The distal end 61, which may be at an angle of 45 degrees, or less, defines a distal end edge 62 as seen best in FIGS. 6 and 9. In the embodiment shown in FIGS. 4-10, the distal tip of the distal end 61 may be cut off or straight at 60. The structure 53 cross members, arms or struts lie in a plane that is substantially parallel to the plane of distal end edge 62. Each of the cross members, arms or struts in this embodiment, include a central straight portion 57 on strut 54 and a straight portion 58 on arm or member 55. Arms or members 54, 55 have at each opposite end of the central portions 57, 58 curved or rounded portions as seen at 59. As seen best in FIGS. 5, 6 and 9, 10 the round portions of the arms or members 54, 55 extend radially outwardly or beyond the cylindrical edge 62 of distal end portion 61 of tube 51.

It will be appreciated by those of ordinary skill in the art that the rounded ends of the cross members or arms 54, 55 will provide a surface that is in contact with the tissue in the oral cavity of the patient but because of the shape will not cause irritation or discomfort. Moreover, the cruciate shape of the cap will prevent the tissue in the patient's mouth from clogging or adhering to the open end of the tube 51 thereby assuring that particles or other detritus to be removed is not impeded. It will also be seen, for example from FIG. 5, that the central portion 57 of arm 54 is spaced from the plane of the edge 62 of distal end 61 of tube 51. It should also be noted that the acute angle of the distal end 61 of tube 51 creates a cross-sectional area that is greater than the transverse cross-sectional area of the tube 51 thereby assuring that the area at the distal end 61 of the tube, notwithstanding the presence of the cross members or arms 54, 55 will not restrict the cross-sectional area of the tube 51 and cap 52 thereby retaining the complete suction (negative) pressure by not restricting the flow area.

Figure 11:
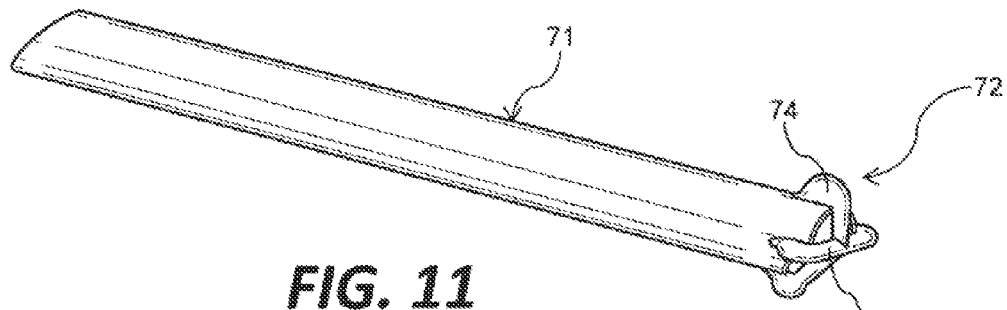
FIG. 11 is a perspective view of a third embodiment of the invention.
Figure 12:
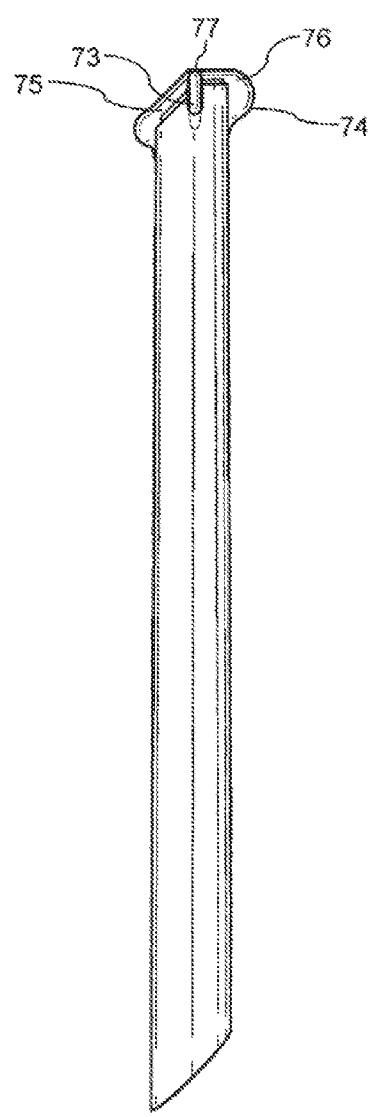
FIG. 12 is a side elevation view of the embodiment shown in FIG. 11.

In another embodiment shown in FIGS. 11 and 12, the cruciate end cap structure 72 of tube 71 also comprises cross members, arms or struts 73, 74. Cross member 74 comprises two segments or bars 75, 76 connected at the intersection with the second cross member 73, one segment 75 comprising a straight bar lying in the plane parallel to the distal end edge and the other end segment bar 76 lying at an obtuse angle thereto as seen in FIG. 12. Accordingly, at the intersection of the segment 75, 76, there is an apex 77 that assists in holding the tissue of the patient's mouth away from the distal end of the tube so as to prevent clogging or plugging injury due to the patient's tongue, cheek or lips while still allowing suction of larger particles.

The foregoing description is provided to enable any person skilled in the relevant art to practice the various embodiments described herein. Thus, the claims are not intended to be limited to the embodiments shown and described herein, but are to be accorded the full scope consistent with the language of the claims, wherein reference to an element in the singular is not intended to mean "one and only one" unless specifically stated, but rather "one or more." All structural and functional equivalents to the elements of the various embodiments described in this disclosure that are known or may become known to those of ordinary skill in the art are expressly incorporated herein by reference and intended to be encompassed by the claims. Nothing disclosed in this application is intended to be dedicated to the public regardless of whether such disclosure is explicitly recited in the claims.

I claim:

1. A dental suction tube including at a distal end a cruciate structure comprising two orthogonal cross members, said suction tube distal end having an edge formed at an acute angle to the longitudinal axis of said tube, said cruciate structure lying substantially in a plane parallel to said distal end edge, each of said cross members extending radially beyond the cylindrical edge of said tube distal end edge, the radial portion beyond the edge of said tube distal end edge having a round shape, the edge of each round shape of said cross members attached to said tube distal end opening.

2. The dental suction tube of claim 1 wherein the cruciate structure is detachably connected to the distal end of said tube.

3. The dental suction tube of claim 1 wherein said cruciate structure is integral with said tube.

4. The dental suction tube of claim 1 wherein said tube and cruciate structure are molded from plastic material.

5. The dental suction tube of claim 4 wherein said plastic material is polyethylene.

6. The dental suction tube of claim 4 wherein said cruciate structure is slightly resilient.

7. The dental suction tube of claim 1 wherein said cross members comprise a central straight portion having a generally rectangular cross-section.

8. The dental suction tube of claim 7 wherein said round portions at each end of said cross members each have a diameter greater than the cross-section of said member 9. The dental suction tube of claim 8 wherein the cross-sectional area of said distal end edge is greater than said tube transverse cross-sectional area.

10. The dental suction tube of claim 9 wherein the lower edge of said straight portion of each cross-member is spaced from the plane of said distal end edge.

11. The dental suction tube of claim 1 wherein one of said cross members comprises two segments connected at the intersection with said second cross member, one segment comprising a straight bar lying in a plane parallel to said distal end edge and the other segment at an obtuse angle to the first segment.

12. The dental suction tube of claim 11 wherein the distal tip of the distal end edge is straight and perpendicular to the longitudinal axis of said tube.

13. A high volume evacuation tube used in dental procedures, connected at a proximal end to flexible tubing that terminates at a vacuum pressure source, the distal end of the tube comprising an edge that is at an acute angle to the longitudinal axis of said tube, said distal end supporting a cap, said cap comprising a structure including a pair of orthogonally arranged struts, said struts attached at their intersection, each said strut having a generally straight shape, the ends of each said strut having a round portion that projects radially outward of the cylindrical wall of the tube, each round portion attached to the distal end of said tube.

14. In a high volume vacuum ejector tube apparatus used in dental procedures, including a vacuum source, flexible tubing in communication with said vacuum source at a proximal end and to a generally, rigid straight tube with a first diameter and cross-sectional area at the distal end, the distal end terminated at an acute angle to the tube axis to form a distal end edge, the improvement comprising a cap connected to the distal end of the tube, the cap having a pair of arms arranged orthogonally to one another connected at their central portions to one another, said arms arranged in a plane parallel to the plane defined by said distal end edge, each arm having a curved portion at each end, each curved portion connected to said tube distal end.

15. The improvement of claim 14 wherein said tube distal end edge is positioned at an angle of 45 degrees to the longitudinal axis of said tube.

16. The improvement of claim 15 wherein said cap is integral with said tube.

17. The improvement of claim 16 wherein said tube and cap are molded of plastic material.

18. The improvement of claim 17 wherein the cross-sectional area of said distal end edge is greater than said tube cross-sectional area.

19. The improvement of claim 18 wherein said arms are in a plane substantially parallel to and spaced from said distal end edge plane of said tube.

20. The improvement of claim 17 formed from semi-resilient plastic material.

21. The improvement of claim 20 wherein the arms have a smooth outer surface whereby the oral tissue of a patient with whom the ejector tube is used by insertion into the patient's oral cavity is not abrasively aggravated.

22. The improvement of claim 14 wherein said tube and cap is disposable.

23. The improvement of claim 14 wherein said angle is less than 45 degrees.

24. The improvement of claim 14 wherein one of said arms comprises two segments connected at the intersection with said second arm, one segment comprising a straight bar lying in the plane parallel to said distal end edge and the other bar at an obtuse angle to said first bar.

25. The improvement of claim 24 wherein said two segment bars are straight.

* * * * *